(12) United States Patent
Satoh

(10) Patent No.: US 7,291,108 B2
(45) Date of Patent: Nov. 6, 2007

(54) ULTRASONIC TRANSMISSION/RECEPTION APPARATUS FOR GENERATING AN IMAGE BASED ON ULTRASONIC ECHOES AND VIBRO-ACOUSTIC SOUNDS

(75) Inventor: Tomoo Satoh, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 433 days.

(21) Appl. No.: 10/939,465

(22) Filed: Sep. 14, 2004

(65) Prior Publication Data

US 2005/0075565 A1    Apr. 7, 2005

(30) Foreign Application Priority Data

Sep. 19, 2003   (JP)   ............... 2003-327070

(51) Int. Cl.
*A61B 8/00*   (2006.01)
*G01N 29/00*  (2006.01)

(52) U.S. Cl. ................ 600/437; 600/443; 73/625

(58) Field of Classification Search ........ 600/437–461; 367/103; 73/625
See application file for complete search history.

(56) References Cited

U.S. PATENT DOCUMENTS

| | | | | |
|---|---|---|---|---|
| 5,402,393 | A * | 3/1995 | Konrad | ............ 367/89 |
| 5,903,516 | A | 5/1999 | Greenleaf et al. | |
| 5,921,928 | A | 7/1999 | Greenleaf et al. | |
| 5,991,239 | A | 11/1999 | Fatemi-Booshehri et al. | |
| 6,440,075 | B1 * | 8/2002 | Averkiou | ............ 600/443 |
| 6,494,839 | B1 * | 12/2002 | Averkiou | ............ 600/443 |
| 6,511,429 | B1 * | 1/2003 | Fatemi et al. | ............ 600/443 |

OTHER PUBLICATIONS

Christensen, D., Ultrasonic Bioinstrumentation, First edition, pp. 149-158, John Wiley & Sons, 1988.*
Bushberg, J.T., The Essential Physics of Medical Imaging, First edition, pp. 396-397, Williams and Wilkins, 1994.*
Sandrin, L. et al., Time-Resolved Pulsed Elastography with Ultrafast Ultrasonic Imaging, 1999, Ultrasonic Imaging, vol. 21, pp. 259-272.*
Mitri, F.G. et al., Chirp Imaging Vibro-Acoustography for Removing the Ultrasound Standing Wave Artifact, Oct. 2005, IEEE Transactions on Medical Imaging, vol. 24, pp. 1249-1255.*

(Continued)

*Primary Examiner*—Lana Le
*Assistant Examiner*—James R. Talman
(74) *Attorney, Agent, or Firm*—Sughrue Mion Pllc.

(57) ABSTRACT

An ultrasonic transmission/reception apparatus which can image both a minute tissue around a bone part in an object and a minute tissue inside the bone, at a high resolution. The apparatus includes a system control unit which controls the synthesizers so that a first ultrasonic wave may be transmitted from one of the transmission elements while its frequency is being swept, and that a second ultrasonic wave may be transmitted from the other transmission element while its frequency is being swept with a predetermined difference frequency held relative to the frequency of the first ultrasonic wave, a signal processing unit which subjects the detection signal of the ultrasonic echo to predetermined signal processing, a signal processing unit which subjects the detection signal of the vibro-acoustic sound to predetermined signal processing, and a display-image arithmetic unit which generates B-mode image data based on the detection signals subjected to the signal processing. The detection signal may be subjected to pulse compression processing.

8 Claims, 15 Drawing Sheets

OTHER PUBLICATIONS

Samuel Calle, et al., "Application of Vibro-Acoustography to Bone Elasticity Imaging", 2001 IEEE Ultrasonics Symposium, pp. 1601-1605.

Mostafa Fatemi, et al. "Ultrasound-Stimulated Vibro-Acoustic Spectrography", Science, vol. 280, Apr. 3, 1998, pp. 82-85.

* cited by examiner

VIBRO-ACOUSTIC SOUND

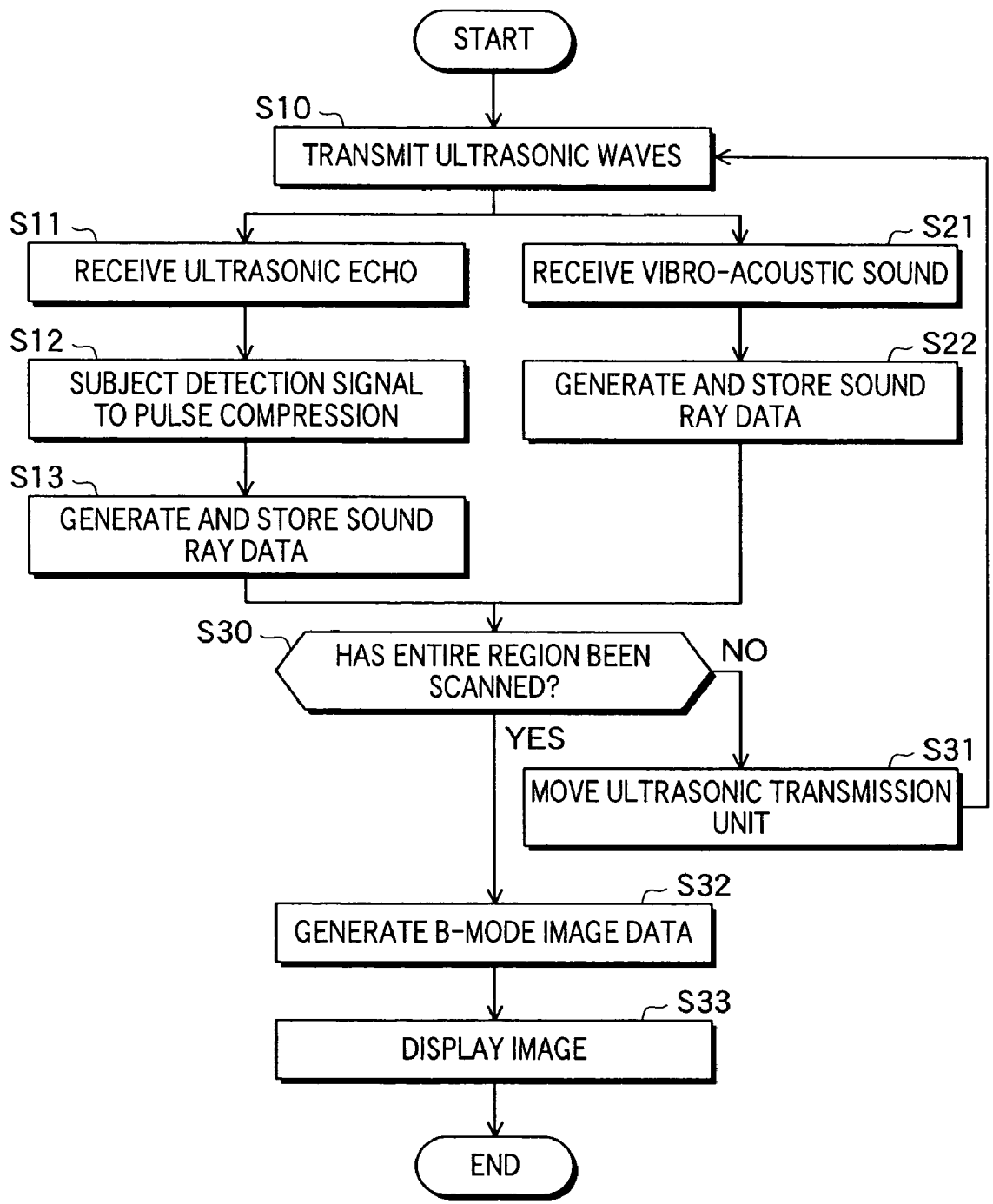

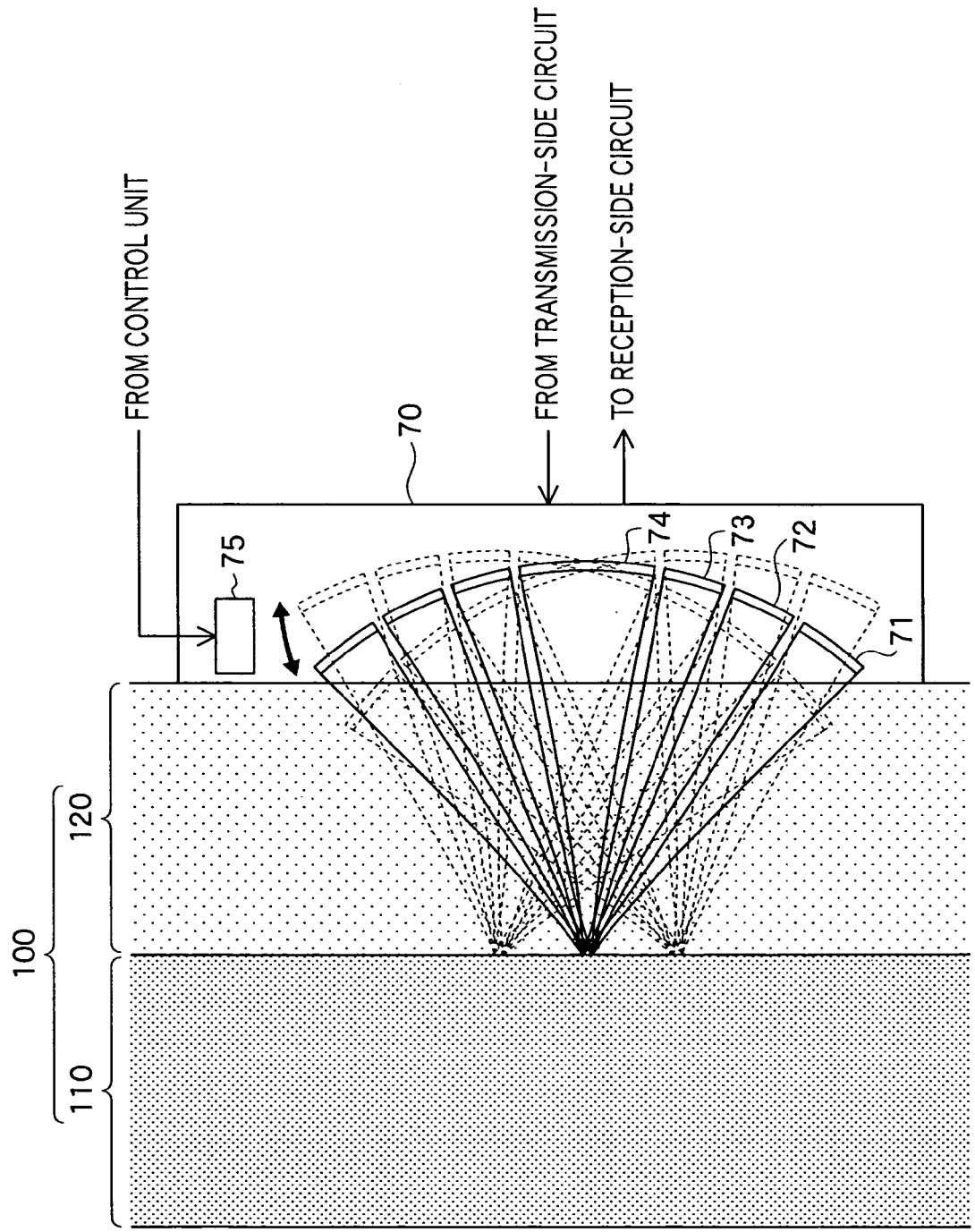

ULTRASONIC TRANSMISSION/RECEPTION APPARATUS FOR GENERATING AN IMAGE BASED ON ULTRASONIC ECHOES AND VIBRO-ACOUSTIC SOUNDS

BACKGROUND OF THE INVENTION

1. Field of the Invention

The present invention relates to an ultrasonic transmission/reception apparatus for use in, for example, making the diagnoses of the internal organs of living bodies by transmitting and receiving ultrasonic waves.

2. Description of a Related Art

In the field of medical treatment, a variety of image technologies have been developed in order to make diagnoses by observing the inner parts of objects to be inspected. Among them, ultrasonic imaging which acquires the internal information of the object by transmitting and receiving ultrasonic waves does not involve exposure to radiation, unlike the other medical image technologies such as X-ray photography and RI (Radio Isotope) scintigraphy. Therefore, ultrasonic imaging is utilized for a fetus diagnosis in an obstetrical region, and in extensive regions including a gynecological region, a circulatory system, a digestive system, etc., as the image technology of high safety.

In ultrasonic imaging, an image is generated by detecting ultrasonic waves which have been reflected at the boundary between substances of different acoustic impedances. Here, in general, an ultrasonic wave has the property of being more easily attenuated at a higher frequency. Therefore, an ultrasonic wave of comparatively high frequency (for example, 5 MHz or so) is employed in case of imaging the shallow part of the object, and an ultrasonic wave of comparatively low frequency (for example, 2 MHz or so) is employed in case of imaging the deep part of the object. Especially in a case where a boundary at which the difference of acoustic impedances is large exists as at a bone part, an ultrasonic wave of comparatively low frequency (for example, 0.5 MHz) is employed.

In case of the two-dimensional array of circular opening, the azimuth resolution $\Delta Y$ of an ultrasonic beam is expressed in terms of a focal distance F, the wavelength $\lambda$ of the ultrasonic wave and the diameter D of the opening, as follows:

$$\Delta Y = 1.22 \times F \times \lambda / D$$

Subject to the same size of the opening, as the wavelength $\lambda$ of the ultrasonic wave is smaller, that is, as the frequency of the ultrasonic wave is higher, the value of $\Delta Y$ becomes smaller, and the azimuth resolution is enhanced more. To the contrary, as the wavelength $\lambda$ of the ultrasonic wave is larger, that is, as the frequency of the ultrasonic wave is lower, the value of $\Delta Y$ becomes larger, and the azimuth resolution degrades more. On the other hand, the size of the opening is limited to a certain size in relation to the size of the object. Therefore, when an ultrasonic wave of low frequency is employed in order to image the deep part of the object, the azimuth resolution degrades, and hence, the minute structure of the deep part such as the interior of a bone cannot be imaged.

It is known that, when an object is irradiated with two ultrasonic waves of slightly different frequencies, vibration which has a frequency corresponding to the difference between the frequencies of the two ultrasonic waves is generated from a part irradiated with the ultrasonic waves. The vibration is also called "vibro-acoustic sound". According to Samuel Calle, et al., "Application of Vibro-Acoustography to Bone Elasticity Imaging", 2001 IEEE Ultrasonics Symposium, pp. 1601-1605, a mechanism for the generation of the vibro-acoustic sound is considered as follows: The vibro-acoustic sound will be generated by (1) the change of an impedance at the examined position of the object, or a radiation pressure based on the absorption and diffusion of the ultrasonic waves, or (2) such a physical phenomenon as the reflection of an ultrasonic beam which is generated by nonlinear interference.

Since such a vibro-acoustic sound has a frequency in an ultrasonic band of an audible range on the order of several kHz—several hundred kHz or so, a signal of sufficient intensity can be acquired even from the vibro-acoustic sound which has passed through a boundary having the large difference of acoustic impedances or has returned from the deep part of the object by way of example. Moreover, since the ultrasonic waves of high frequencies are employed in generating the vibro-acoustic sound, a high resolution can be realized by defining a scan region based on vibro-acoustic sounds. In the above thesis, therefore, it is described that the interior of a bone extracted from the object is imaged by employing the vibro-acoustic sounds. In Fatemi and Greenleaf, "Ultrasound-Stimulated Vibro-Acoustic Spectrography", SCIENCE, Vol. 280, Apr. 3, 1998, pp. 82-85, it is described to image the minute structure of the deep part of the object. Further, in U.S. Pat. No. 5,903,516, it is disclosed to receive vibro-acoustic sounds in an audible range. Furthermore, in U.S. Pat. No. 5,991,239, it is disclosed that, in order to generate vibro-acoustic sounds, electronic scans are performed using a multi-ring annular array or a plurality of ultrasonic transducers.

However, continuous ultrasonic waves which are extraordinarily larger in the number of continuous waves than in case of ordinary ultrasonic imaging must be transmitted in order to generate vibro-acoustic sounds which have the number of continuous waves as required for generating an ultrasonic image. As a result, the distance resolution of detection data on the outer side of a bone part, namely, the shallow part of the object degrades drastically.

SUMMARY OF THE INVENTION

The present invention has for its object to provide an ultrasonic transmission/reception apparatus which can image both a minute tissue around a bone part in an object to be inspected and a minute tissue inside the bone, at a high resolution.

In order to accomplish the object, an ultrasonic transmission/reception apparatus according to the invention comprises first and second ultrasonic transmission means for operating in accordance with a plurality of applied drive signals, respectively; drive-signal generation means for generating the drive signals which are respectively applied to the first and second ultrasonic transmission means; control means for controlling the drive-signal generation means so that a first ultrasonic wave is transmitted from the first ultrasonic transmission means while its frequency is being swept, and that a second ultrasonic wave is transmitted from the second ultrasonic transmission means while its frequency is being swept with a predetermined difference frequency held relative to a frequency of the first ultrasonic wave; first reception means for receiving an ultrasonic echo caused by reflection of the first or second ultrasonic wave in an object to be inspected; second reception means for receiving an acoustic wave or an ultrasonic wave which has been generated from a predetermined region within the object by projecting the first and second ultrasonic waves toward the region, and which has a frequency corresponding to a difference frequency between frequencies of the first and second ultrasonic waves, so as to output a detection signal; first signal processing means for subjecting a detection signal outputted from the first reception means, to predetermined signal processing; second signal processing means for subjecting the detection signal outputted from the second reception means, to predetermined signal processing; and image data generation means for generating image data representative of an ultrasonic image, on the basis of the detection signals subjected to the signal processing by the first and/or second signal processing means.

According to the present invention, ultrasonic image data on the deep part of the object are generated on the basis of the vibro-acoustic sound generated using the first and second ultrasonic waves, and ultrasonic image data on the shallow part of the object are generated on the basis of the ultrasonic echo corresponding to the first or second ultrasonic wave. On that occasion, the first and second ultrasonic waves are transmitted while their frequencies are being swept with the predetermined difference frequency held, and the detection signal on the ultrasonic echo corresponding to the ultrasonic waves is processed. Thus, the ultrasonic image data of high resolution can be generated for both the shallow part and deep part of the object.

BRIEF DESCRIPTION OF THE DRAWINGS

FIG. 4 is a flow chart showing an ultrasonic transmission/reception method according to the first embodiment of the invention;

FIG. 13 is a diagram showing part of an ultrasonic transmission/reception apparatus according to the fifth embodiment of the invention;

DESCRIPTION OF THE EXEMPLARY EMBODIMENTS

Figure 1:
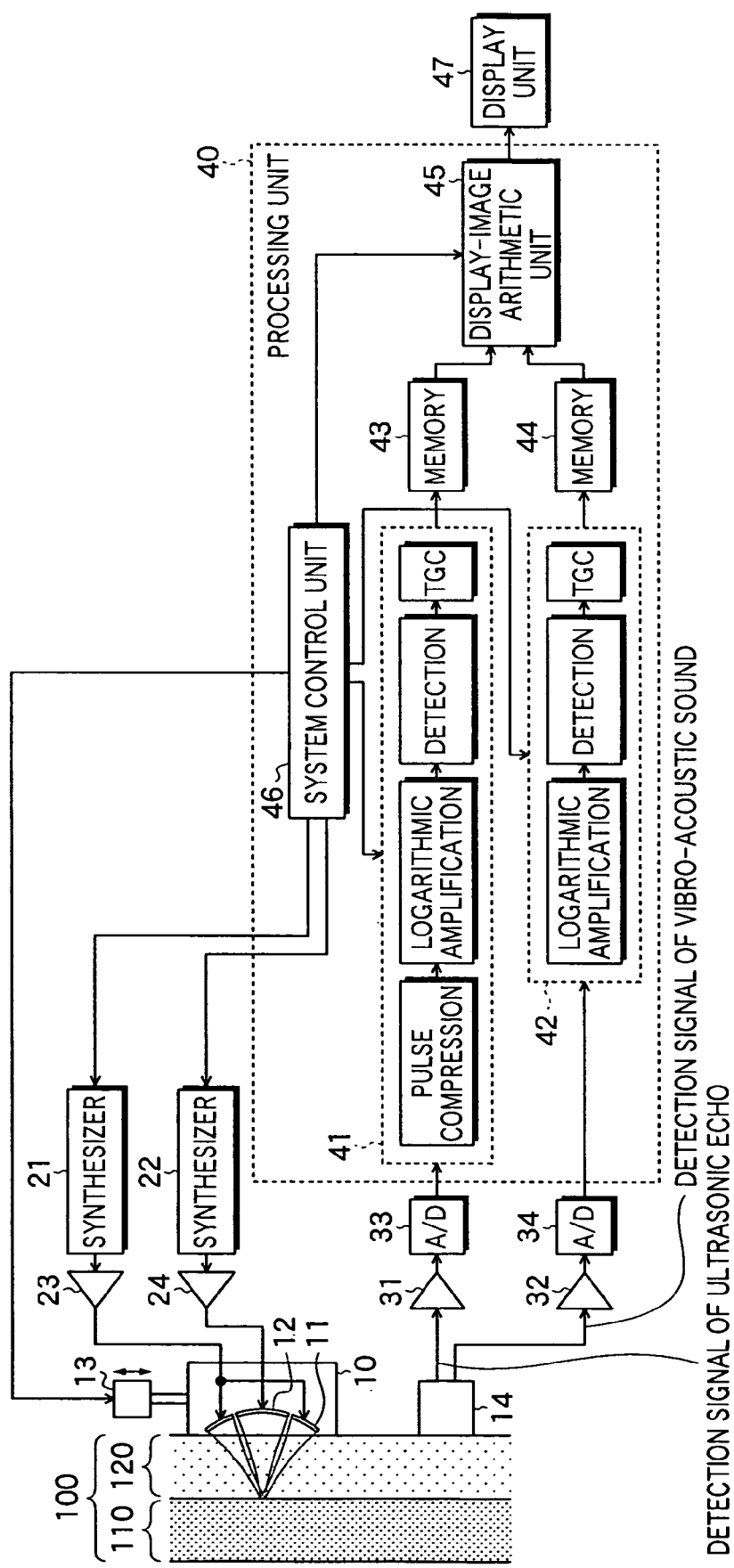
FIG. 1 is a block diagram showing the configuration of an ultrasonic transmission/reception apparatus according to the first embodiment of the invention.

Now, exemplary embodiments for carrying out the present invention will be described in detail with reference to the drawings. Incidentally, identical reference numerals are assigned to the same constituents, which shall be omitted from description.

FIG. 1 is a block diagram showing the configuration of an ultrasonic transmission/reception apparatus according to the first embodiment of the invention. The ultrasonic transmission/reception apparatus is an apparatus which transmits ultrasonic waves and receives ultrasonic echoes from an object to be inspected so as to image the ultrasonic echoes, and which generates vibro-acoustic sounds in the object and receives the vibro-acoustic sounds so as to image the vibro-acoustic sounds.

Figure 2:
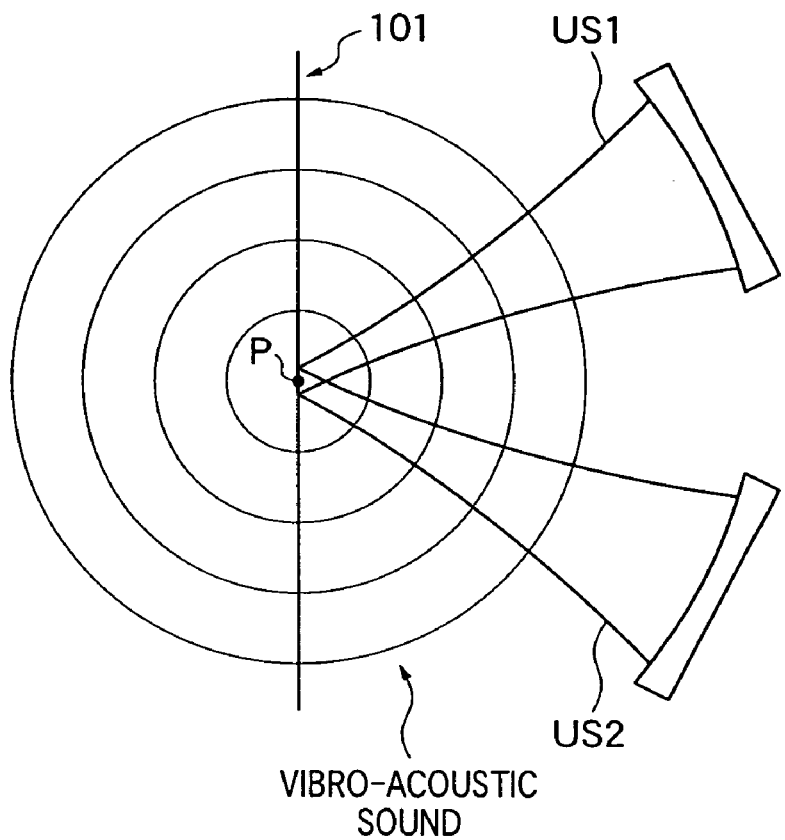
FIG. 2 is a diagram showing a situation where a vibro-acoustic sound is generated.

First, the vibro-acoustic sound will be explained. As shown in FIG. 2, when two ultrasonic beams US1 and US2 whose frequencies are slightly different are transmitted toward an object 101, vibration occurs in a region P irradiated with the two ultrasonic waves (this phenomenon is also termed "vibro-acoustic phenomenon"). The vibration generates an acoustic wave (or ultrasonic wave) called "vibro-acoustic sound". The wave fronts of the vibro-acoustic sound are depicted in FIG. 2. The vibro-acoustic sound has a frequency (in, for example, the audible range on the order of several kHz—an ultrasonic band on the order of several hundred kHz) which corresponds to the difference frequency of the two ultrasonic waves US1 and US2. In this manner, the vibro-acoustic sound has the frequency which is lower as compared with those of ultrasonic waves generally employed for ultrasonic imaging, so that it is easy of arriving at the deeper part of the object (or it has a good penetrability). Moreover, since the acoustic wave (or ultrasonic wave) of such a low frequency is formed by transmitting the ultrasonic waves of high frequencies, a beam spot which is finer as compared with one in the case of directly transmitting an ultrasonic wave of low frequency can be formed. Furthermore, since the generation intensity of the vibro-acoustic sound and the frequency characteristic of generation intensities change in accordance with the characteristics of the region P including the property thereof, the property of the vibro-acoustic sound generation region can be imaged by generating image data on the basis of the intensity of the vibro-acoustic sounds. That is, an ultrasonic image in which a high resolution and the favorable penetrability into the object are compatible can be generated by employing the vibro-acoustic sounds.

As shown in FIG. 1, the ultrasonic transmission/reception apparatus includes an ultrasonic transmission unit 10 which is used in touch with an object 100, a mechanical stage 13, and a reception unit 14.

The ultrasonic transmission unit 10 includes transmission elements 11 and 12. Each of the transmission elements 11 and 12 is constructed of an ultrasonic transducer in which electrodes are formed on both the ends of a piezoelectric element made of a ceramic piezoelectric material such as PZT (Pb (lead) zirconate titanate), or a high-polymer piezoelectric material such as PVDF (polyvinylidene difluoride). When a voltage is applied across the electrodes of such an ultrasonic transducer by sending a continuous-wave drive signal thereto, the piezoelectric element is expanded or contracted. Owing to the expansion and contraction, an ultrasonic wave is generated from each ultrasonic transducer.

The transmission element 11 has an annular shape, while the transmission element 12 has a circular shape. Alternatively, the transmission element 12 may well have an annular shape. The transmission elements 11 and 12 are concentrically arranged to constitute a coaxial annular array. Incidentally, the sections of the transmission elements 11 and 12 are depicted in the ultrasonic transmission unit 10 shown in FIG. 1. Owing to such an arrangement of the transmission elements, a plurality of ultrasonic beams transmitted from the different transmission elements 11 and 12 can be focused at an identical depth in an identical direction.

The mechanical stage 13 mechanically drives the annular array including the transmission elements 11 and 12, whereby the ultrasonic waves to be transmitted are caused to linearly scan the object 100.

The reception unit 14 has a plurality of reception elements that are made of PZT or the like, and is a hydrophone that receives an ultrasonic echo and a vibro-acoustic sound from the object so as to output detection signals, respectively. Each of the reception elements is expanded or contracted by receiving the ultrasonic echo or vibro-acoustic sound from the object 100, and it generates an electric signal corresponding to the intensity of the received ultrasonic echo or vibro-acoustic sound. Such electric signals are outputted as the detection signals of the ultrasonic echo or vibro-acoustic sound.

Figure 3:
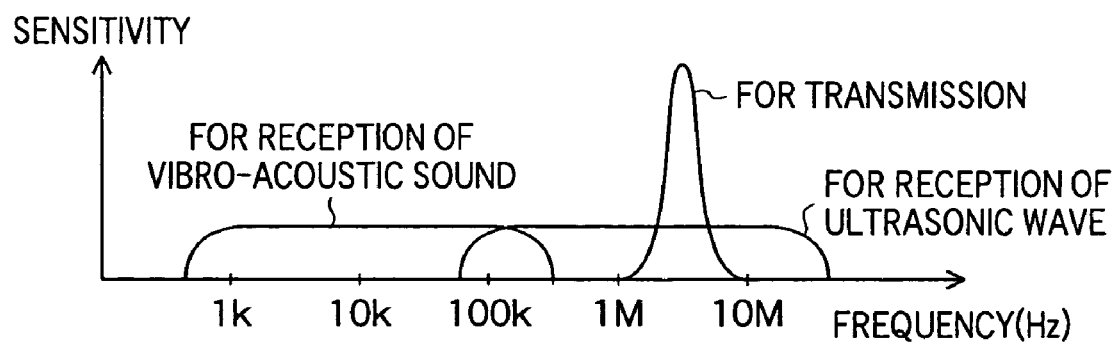
FIG. 3 is a diagram showing the frequency characteristics of transmission elements and reception elements.

FIG. 3 shows the frequency characteristics of the transmission elements and reception elements which are used in the ultrasonic transmission/reception apparatus according to this embodiment. As shown in FIG. 3, the transmission elements 11 and 12 included in the ultrasonic transmission unit 10 are set so as to have the highest sensitivity in a megahertz band (for example, 3 MHz-10 MHz). Besides, the reception element for receiving the ultrasonic wave as is included in the reception unit 14 has a substantially constant reception sensitivity in a frequency band of several tens kHz—several tens MHz. On the other hand, the reception element for receiving the vibro-acoustic sound as is included in the reception unit 14 has a substantially constant reception sensitivity in a frequency band of several hundred Hz—several hundred kHz.

Referring to FIG. 1 again, the ultrasonic transmission/reception apparatus includes synthesizers 21 and 22, power amplifiers 23 and 24, preamplifiers 31 and 32, and A/D converters 33 and 34. The synthesizers 21 and 22 generate drive signals to be respectively applied to the transmission elements 11 and 12, under the control of a system control unit 46 to be stated later. The power amplifiers 23 and 24 power-amplify the continuous-wave drive signals respectively generated by the synthesizers 21 and 22.

The preamplifiers 31 and 32 pre-amplify the detection signals (detection signal of the ultrasonic echo and detection signal of the vibro-acoustic sound) outputted from the reception unit 14, respectively. Besides, the A/D converters 33 and 34 convert the analog detection signals amplified by the preamplifiers 31 and 32, into digital detection signals (detection data of the ultrasonic echo and detection data of the vibro-acoustic sound), respectively.

In addition, the ultrasonic transmission/reception apparatus includes a processing unit 40, and a display unit 47.

The processing unit 40 is a data processor, for example, a personal computer. It includes signal processing units 41 and 42, memories 43 and 44, a display-image arithmetic unit 45, and the system control unit 46.

The signal processing unit 41 executes signal processing, such as pulse compression, logarithmic amplification, detection and TGC (Time Gain Compensation), for the detection data of the ultrasonic echo inputted from the A/D converter 33. Besides, the signal processing unit 42 executes signal processing, such as logarithmic amplification, detection and TGC amplification, for the detection data of the vibro-acoustic sound inputted from the A/D converter 34. Thus, sound ray data which correspond to the ultrasonic echo and the vibro-acoustic sound received from the reception unit 14 are generated. The memories 43 and 44 store the generated sound ray data in predetermined storage areas. The sound ray data respectively stored in the memories 43 and 44 constitute surface data which represent one section in the object.

The display-image arithmetic unit 45 converts a scan format for the sound ray data (surface data) respectively stored in the memories 43 and 44, thereby to generate B-mode image data. The system control unit 46 controls the units 41-45 of the processing unit 40, and it also controls the frequencies and generation times of the drive signals which the synthesizers 21 and 22 generate. Besides, the system control unit 46 controls the mechanical stage 13 so that the desired region of the object 100 may be scanned with the ultrasonic waves transmitted from the ultrasonic transmission unit 10.

The display unit 47 is a display device, for example, a CRT or an LCD, and it displays an ultrasonic image on the basis of the B-mode image data generated by the display-image arithmetic unit 45.

Next, an ultrasonic transmission/reception method according to the first embodiment of the invention will be described with reference to FIG. 1 and FIG. 5A-FIG. 7C. FIG. 4 is a flow chart showing the ultrasonic transmission/reception method according to this embodiment.

Figure 5A:
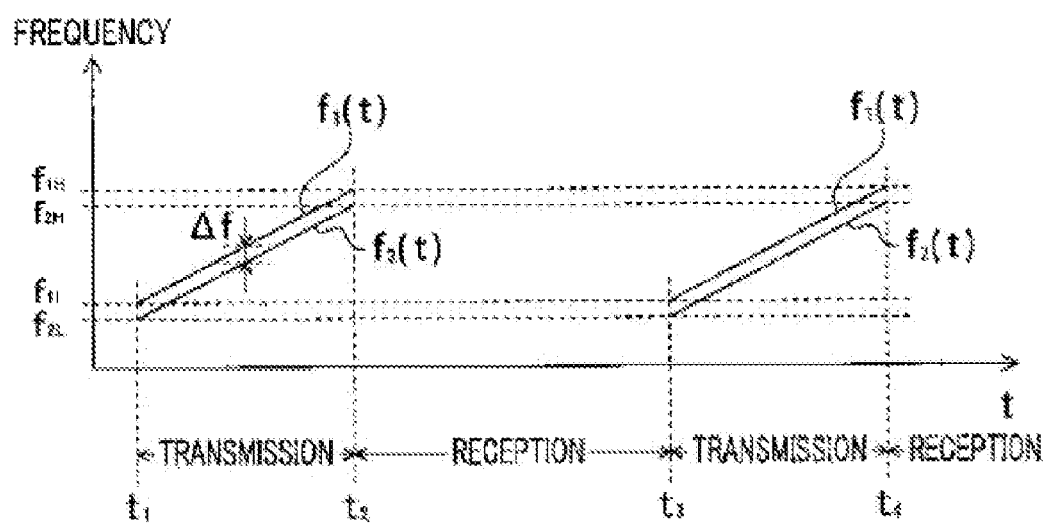
FIG. 5A is a diagram showing temporal changes in the frequencies of transmitted ultrasonic waves.
Figure 5B:
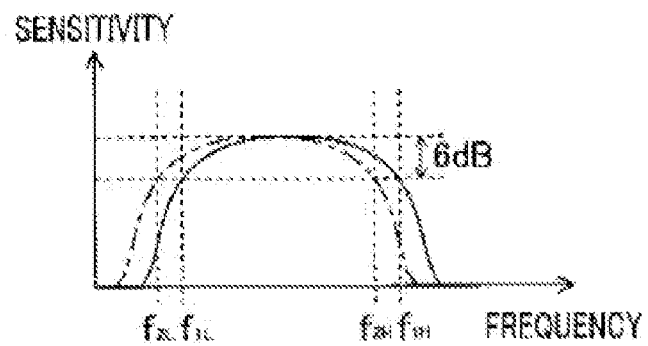
FIG. 5B is a diagram showing the relationship between a transmission frequency and the band of an ultrasonic transducer.

At a step S10 in FIG. 4, the ultrasonic transmission/reception apparatus shown in FIG. 1 transmits ultrasonic waves respectively having different frequencies, from the transmission elements 11 and 12 of the ultrasonic transmission unit 10 so as to focus the ultrasonic waves on the surface of the bone part 110 of the object 100. FIG. 5A shows temporal changes in the frequencies of the ultrasonic waves which are transmitted from the transmission elements 11 and 12. As shown in FIG. 5A, in this embodiment, the ultrasonic waves are transmitted while the frequencies are being swept over transmission times t1-t2. More specifically, a chirp waveform having a frequency f1(t) which changes from a value f1L to a value f1H rectilinearly with time is transmitted from the transmission element 11, while a chirp waveform having a frequency f2(t) which changes from a value f2L to a value f2H rectilinearly with time is transmitted from the transmission element 12. On that occasion, the difference $\Delta f = f1(t) - f2(t)$ between the frequencies of the two ultrasonic waves is always held constant. Besides, the transmission period Tx of the ultrasonic waves is set at (1 through 10)×(1/Δf) in order that there is at least one cycle of the vibro-acoustic sound present during the transmission period (for example, 1 through 10). Here, the transmission elements 11 and 12 should desirably be the ultrasonic transducers whose bandwidths affording −6 dB correspond to f1L-f1H and f2L-f2H as shown in FIG. 5B, respectively.

Figure 6:
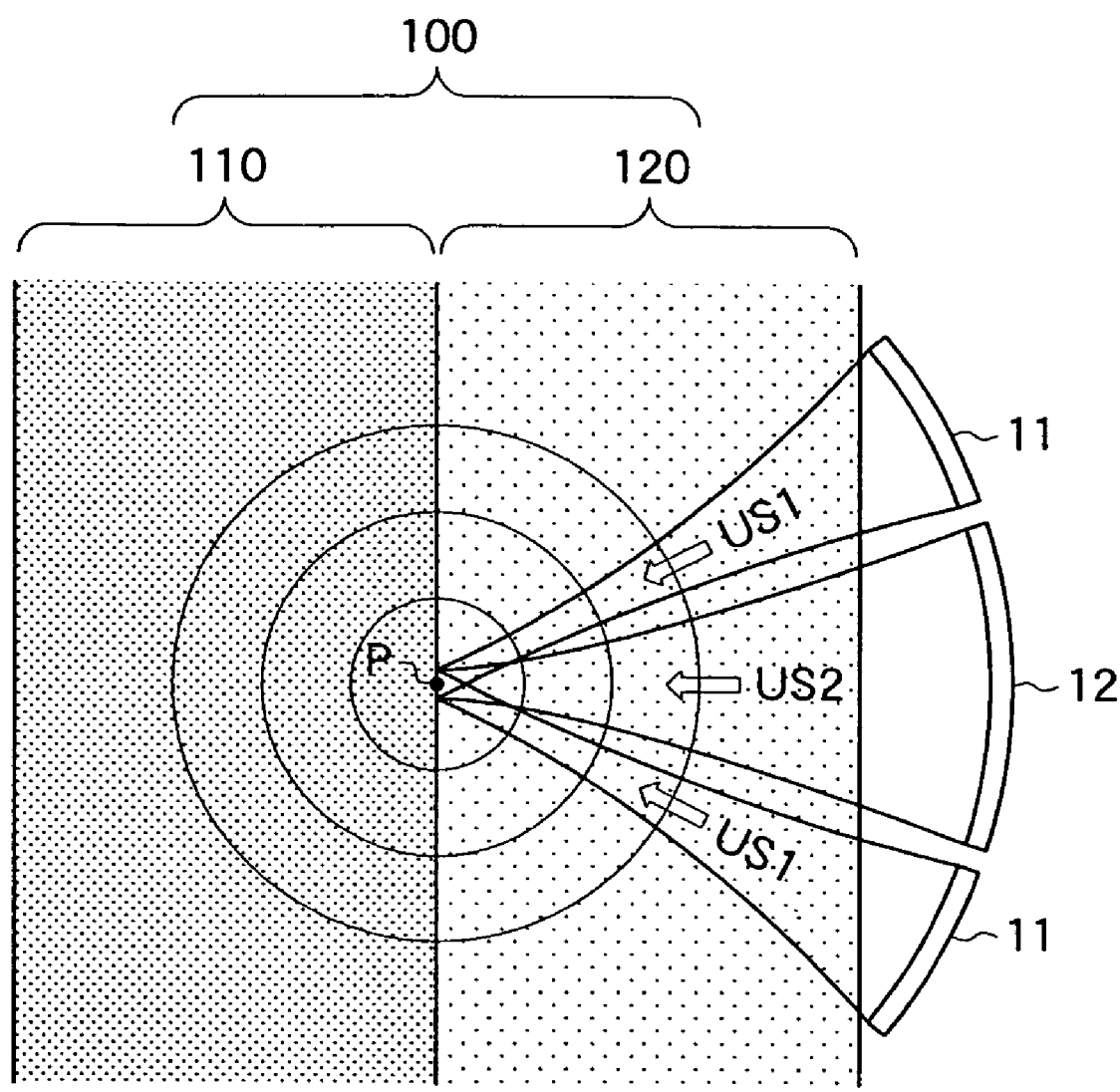
FIG. 6 is a diagram showing a situation where ultrasonic waves are transmitted from the transmission elements.

Thus, as shown in FIG. 6, the ultrasonic wave US1 having the frequency f1(t) is transmitted from the transmission element 11, and the ultrasonic wave US2 having the frequency f2(t) is transmitted from the transmission element 12.

At the surface of the bone part 110 of the object 100, the ultrasonic waves US1 and US2 are reflected toward a soft tissue 120 in the object 100, whereby ultrasonic echoes having the frequencies f1(t) and f2(t) are generated. Since the difference between the frequencies of the ultrasonic echoes is small as compared with the frequencies of the ultrasonic echoes, it can be said that an ultrasonic echo having a substantially single frequency $f1(t) \approx f2(t)$ is generated. Besides, the ultrasonic waves US1 and US2 are focused on the region P of the surface of the bone part 110. Thus, the vibro-acoustic sound having an intensity which corresponds to the frequency Δf and the characteristics of the region P including the property thereof is generated from the region P. In FIG. 6, concentric circles around the region P represent the wave fronts of the vibro-acoustic sound. The vibro-acoustic sound generated from the region P propagates within the bone part 110 and the soft tissue 120.

At a step S11 in FIG. 4, the reception unit 14 receives the ultrasonic echo. The detection signal of the ultrasonic echo is pre-amplified in the preamplifier 31 and is converted into a digital signal (detection data of the ultrasonic echo) in the A/D converter 33, whereupon the digital signal is inputted to the signal processing unit 41.

At a step S12, the signal processing unit 41 correlates the detection data of the inputted ultrasonic echo with the waveform of the ultrasonic wave US1 or US2, thereby to perform pulse compression processing. Here, in this embodiment, continuous ultrasonic waves having significantly longer transmission periods that are used in ordinary ultrasonic imaging are transmitted in order to generate the vibro-acoustic sound. Accordingly, when an ultrasonic image is formed on the basis of the ultrasonic echoes corresponding to such continuous ultrasonic waves, a distance resolution concerning a depth direction lowers. In this embodiment, therefore, the ultrasonic waves US1 and US2 are transmitted with their frequencies swept, and the ultrasonic echoes corresponding to them are subjected to the pulse compression, thereby to enhance the distance resolution.

At a step S13, the signal processing unit 41 subjects the detection data of the pulse-compressed ultrasonic echo to predetermined signal processing such as detection, thereby to generate sound ray data corresponding to the received ultrasonic echo. The sound ray data are stored in the predetermined storage area of the memory 43 in accordance with the control of the system control unit 46.

On the other hand, at a step S21, the reception unit 14 receives the vibro-acoustic sound having propagated from the region P and outputs the detection signal of the vibro-acoustic sound. The detection signal of the vibro-acoustic sound is pre-amplified in the preamplifier 32 and is converted into a digital signal (detection data of the vibro-acoustic sound) in the A/D converter 34, whereupon the digital signal is inputted to the signal processing unit 42. On that occasion, in consideration of the attenuation value of the vibro-acoustic sound during the propagation thereof, an intensity correction corresponding to the propagation distance should desirably be made for the detection signal of the vibro-acoustic sound. For that purpose, by way of example, the gain of the preamplifier 32 may be regulated in accordance with the distance between the region P and the reception unit 14, under the control of the system control unit 46.

At a step S22, the signal processing unit 42 subjects the detection data of the inputted vibro-acoustic sound to predetermined signal processing such as detection. Thus, sound ray data which represent the intensity of the received vibro-acoustic sound are generated. The sound ray data are stored in the predetermined storage area of the memory 44 in accordance with the control of the system control unit 46.

In a case where, at a step S30, any region to be scanned remains in the object 100, the mechanical stage 13 moves the ultrasonic transmission unit 10 in accordance with the control of the system control unit 46 (step S31). Further, the ultrasonic transmission/reception apparatus transmits the ultrasonic waves US1 and US2 and receives an ultrasonic echo and a vibro-acoustic sound, so as to accumulate the sound ray data of the ultrasonic echo and vibro-acoustic sound (steps S10-S13 and steps S21-S22).

Figure 7A:
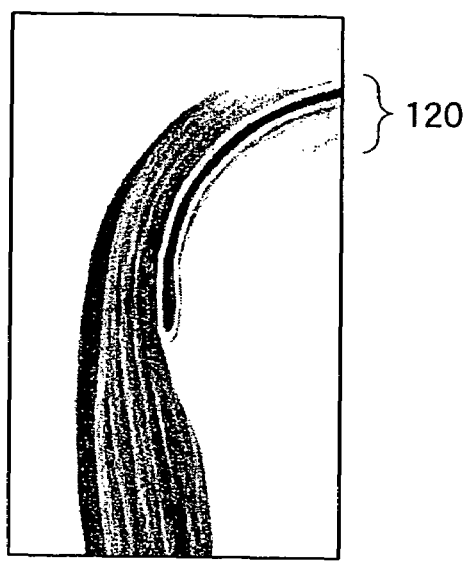
FIG. 7A is a diagram showing an ultrasonic image which represents a soft tissue outside a bone part as imaged by the ultrasonic transmission/reception apparatus according to the first embodiment of the invention.
Figure 7B:
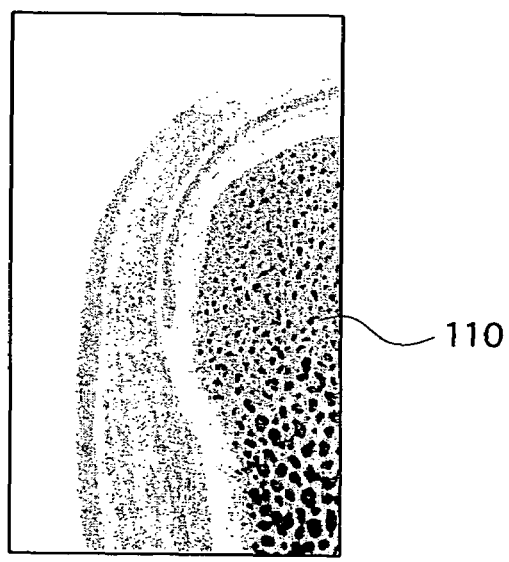
FIG. 7B is a diagram showing an ultrasonic image which represents the internal tissue of the bone part as imaged by the ultrasonic transmission/reception apparatus according to the first embodiment of the invention.

In contrast, in a case where the entire region to be scanned in the object 100 has been scanned at the step S30, the routine proceeds to a step S32, at which the display-image arithmetic unit 45 generates B-mode image data on the basis of the sound ray data respectively stored in the memories 43 and 44. Thus, as shown in FIG. 7A, the B-mode image data are obtained on the basis of the sound ray data of the ultrasonic echoes as stored in the memory 43, and an ultrasonic image representing the soft tissue 120 outside the bone part 110 is generated from the obtained B-mode image data. Besides, as shown in FIG. 7B, the B-mode image data are obtained on the basis of the sound ray data of the vibro-acoustic sounds as stored in the memory 44, and an ultrasonic image representing the internal tissue of the bone part 110 is generated from the obtained B-mode image data.

Figure 7C:
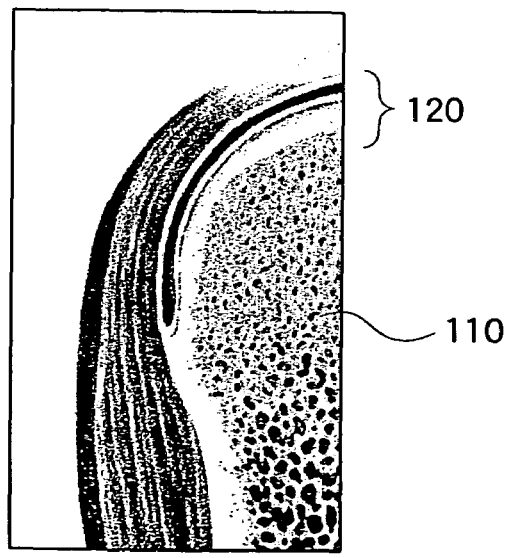
FIG. 7C is a diagram showing a composite ultrasonic image which represents both the soft tissue outside the bone part and the internal tissue of the bone part.

At a step S33, the display-image arithmetic unit 45 causes the display unit 47 to display an ultrasonic image which is expressed by the generated B-mode image data. On that occasion, the display-image arithmetic unit 45 may well cause the display unit 47 to successively display the ultrasonic images shown in FIGS. 7A and 7B. Alternatively, as shown in FIG. 7C, the display-image arithmetic unit 45 may well composite the ultrasonic images so as to display the ultrasonic image which represents both the soft tissue outside the bone part and the internal tissue of the bone part.

In this embodiment, the transmission elements and reception elements which have the frequency characteristics as shown in FIG. 3 have been employed. However, these elements are not restrictive, but transmission elements and reception elements having frequency characteristics shown in FIG. 8 may well be employed by way of example.

Figure 8:
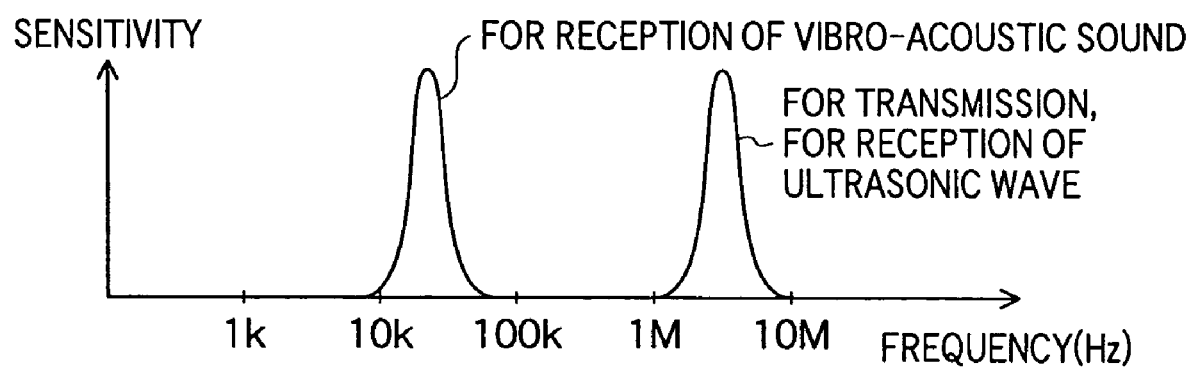
FIG. 8 is a diagram showing the other frequency characteristics of the transmission elements and reception elements which are used in the ultrasonic transmission/reception apparatus according to the first embodiment of the invention.

In general, the frequencies of ultrasonic waves which can generate a vibro-acoustic sound differ depending upon the characteristics of a region including the property thereof, from which the vibro-acoustic sound is to be generated. Therefore, in a case where the characteristics of the object or sample are unknown (as in, for example, researches), it is desirable to employ a reception element which can receive an acoustic wave or ultrasonic wave in a wide band. Therefore, this embodiment has employed the reception element of non-resonance type which has a low detection sensitivity, but which has a wide detectable frequency band, as shown in FIG. 3. However, in a case where the characteristics of the object or sample are known (as in, for example, an examination of specified use), it is more advantageous to heighten a detection sensitivity by employing a reception element of narrower bandwidth. Therefore, in a case where the characteristics of the object are known to some extent, that is, in a case where the spectrum of a vibro-acoustic sound is definite and where the range thereof is considered not to change greatly, it is desirable to receive the vibro-acoustic sound by employing a reception element of resonance type which has a narrow band, but which has a high sensitivity, as shown in FIG. 8. Simultaneously, regarding also a reception element for receiving an ultrasonic echo, it is desirable to heighten a sensitivity by employing a reception element of resonance type which has frequency characteristics in substantially the same range as that of transmitted ultrasonic waves.

Besides, the detection signals of the vibro-acoustic sound and the ultrasonic echo may well be respectively subjected to filtering processes which pass these signals through predetermined frequency bands. Thus, unnecessary bands in the detection signals can be removed to heighten the S/N ratios of these signals.

Next, an ultrasonic transmission/reception apparatus according to the second embodiment of the invention will be described.

Figure 9:
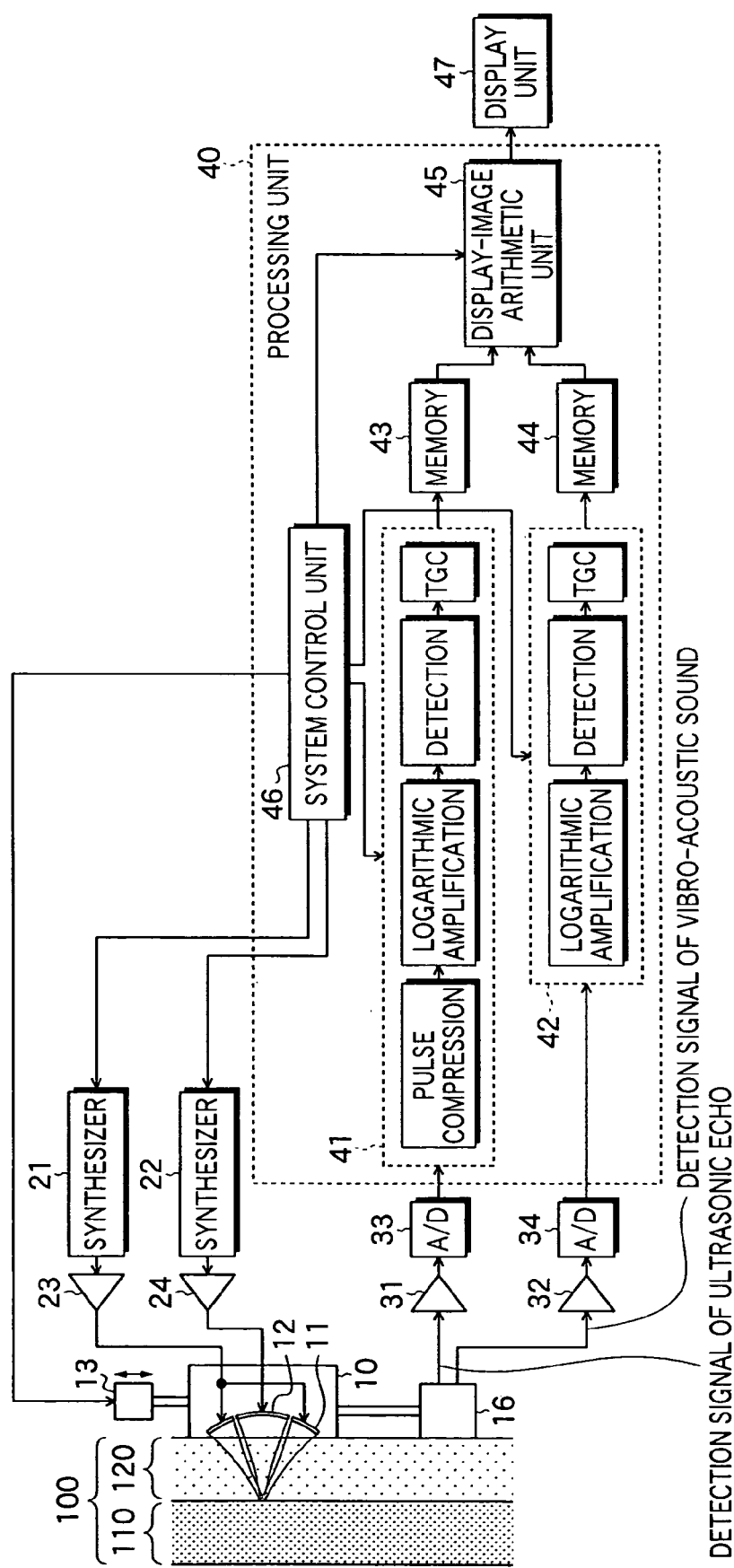
FIG. 9 is a block diagram showing the configuration of an ultrasonic transmission/reception apparatus according to the second embodiment of the invention.

The ultrasonic transmission/reception apparatus according to this embodiment shown in FIG. 9 has a reception unit 16 which is mechanically connected with an ultrasonic transmission unit 10. The remaining configuration is the same as in the ultrasonic transmission/reception apparatus shown in FIG. 1.

Here, the intensity of a vibro-acoustic sound generated in the object represents the property of a region where the vibro-acoustic sound has been generated. However, the vibro-acoustic sound attenuates during its propagation within the object, likewise to an ultrasonic wave. Accordingly, when the positional relationship between the generation region of the vibro-acoustic sound and the reception unit changes, the attenuation rate of the vibro-acoustic sound changes, and hence, the precision of information on the vibro-acoustic sound generation region lowers.

In the ultrasonic transmission/reception apparatus according to this embodiment, therefore, when the ultrasonic transmission unit 10 is moved by the drive of a mechanical stage 13, the reception unit 16 is moved together. Thus, the positional relationship between the focus of two ultrasonic waves US1 and US2 transmitted from the ultrasonic transmission unit 10, namely, the vibro-acoustic sound generation region, and the reception unit 16 is always held constant. Accordingly, the attenuation rate is substantially constant. In the processing of the detection signal of the vibro-acoustic sound, therefore, it becomes unnecessary to make an intensity correction corresponding to the distance between the generation region of the vibro-acoustic sound and the reception unit 16.

Next, an ultrasonic transmission/reception apparatus according to the third embodiment of the invention will be described.

Figure 10:
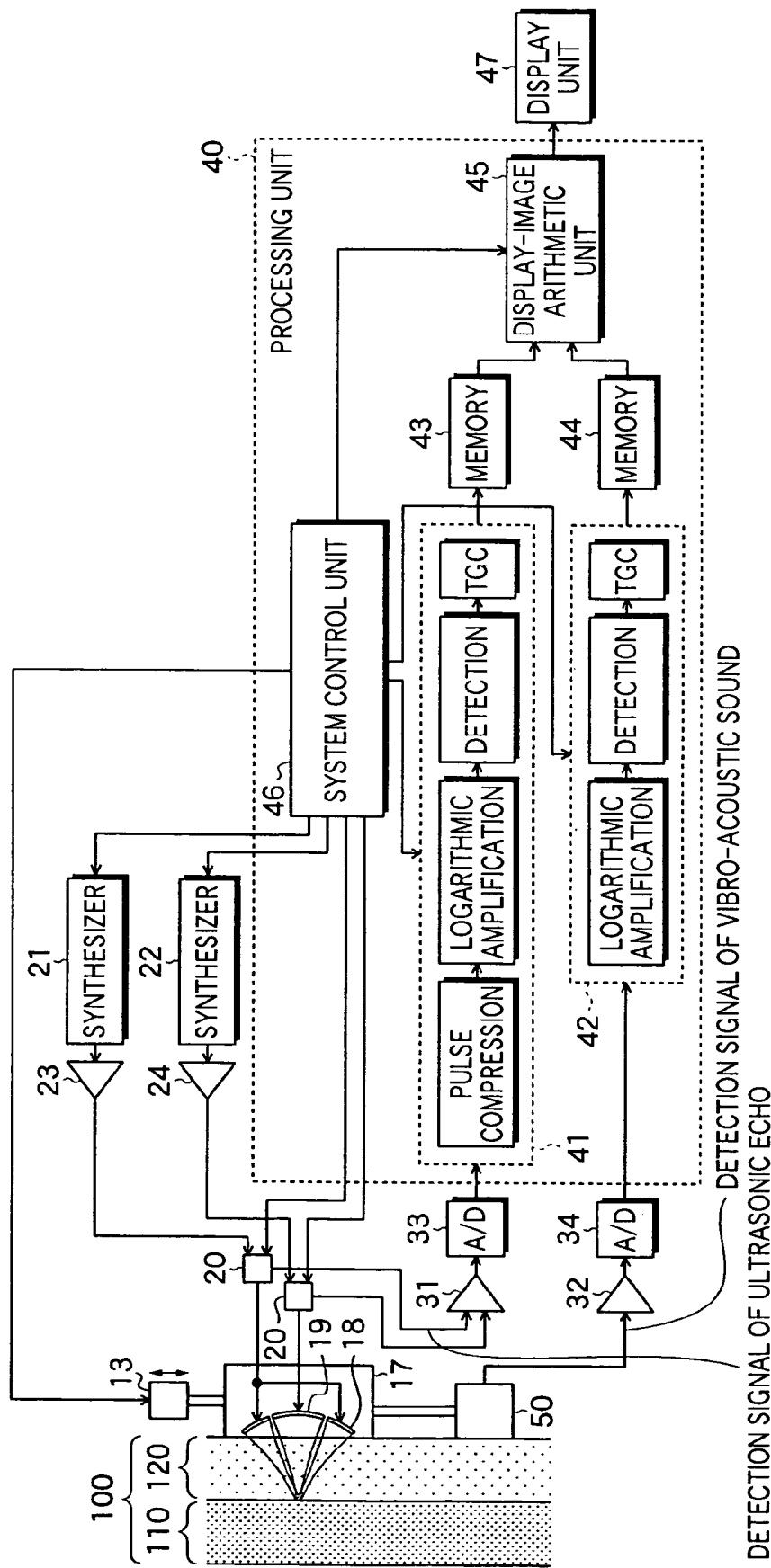
FIG. 10 is a block diagram showing the configuration of an ultrasonic transmission/reception apparatus according to the third embodiment of the invention.

The ultrasonic transmission/reception apparatus shown in FIG. 10 includes an ultrasonic transmission/reception unit 17 which transmits and receives ultrasonic waves, transmission/reception changeover units 20, and a reception unit 50 which receives a vibro-acoustic sound, instead of the ultrasonic transmission unit 10 and reception unit 16 shown in FIG. 9. The ultrasonic transmission/reception unit 17 includes ultrasonic transducers 18 and 19 as elements which both transmit ultrasonic waves and receive ultrasonic echoes. The remaining configuration is the same as in the ultrasonic transmission/reception apparatus shown in FIG. 9.

The ultrasonic transducers 18 and 19 transmit the ultrasonic waves having frequencies different from each other, respectively, thereby to generate a vibro-acoustic sound, and they receive the ultrasonic echoes generated by the reflections of the ultrasonic waves from a soft tissue 120 within the object 100. Besides, the transmission/reception changeover units 20 change-over the transmissions of the ultrasonic waves and the receptions of the ultrasonic echoes in the ultrasonic transducers 18 and 19, in accordance with the control of a system control unit 46. Further, the reception unit 50 receives the vibro-acoustic sound.

According to the ultrasonic transmission/reception apparatus of this embodiment, the ultrasonic transducers for the transmissions of the ultrasonic waves are employed also for the receptions, whereby the ultrasonic echoes can be received at a high sensitivity.

Figure 11:
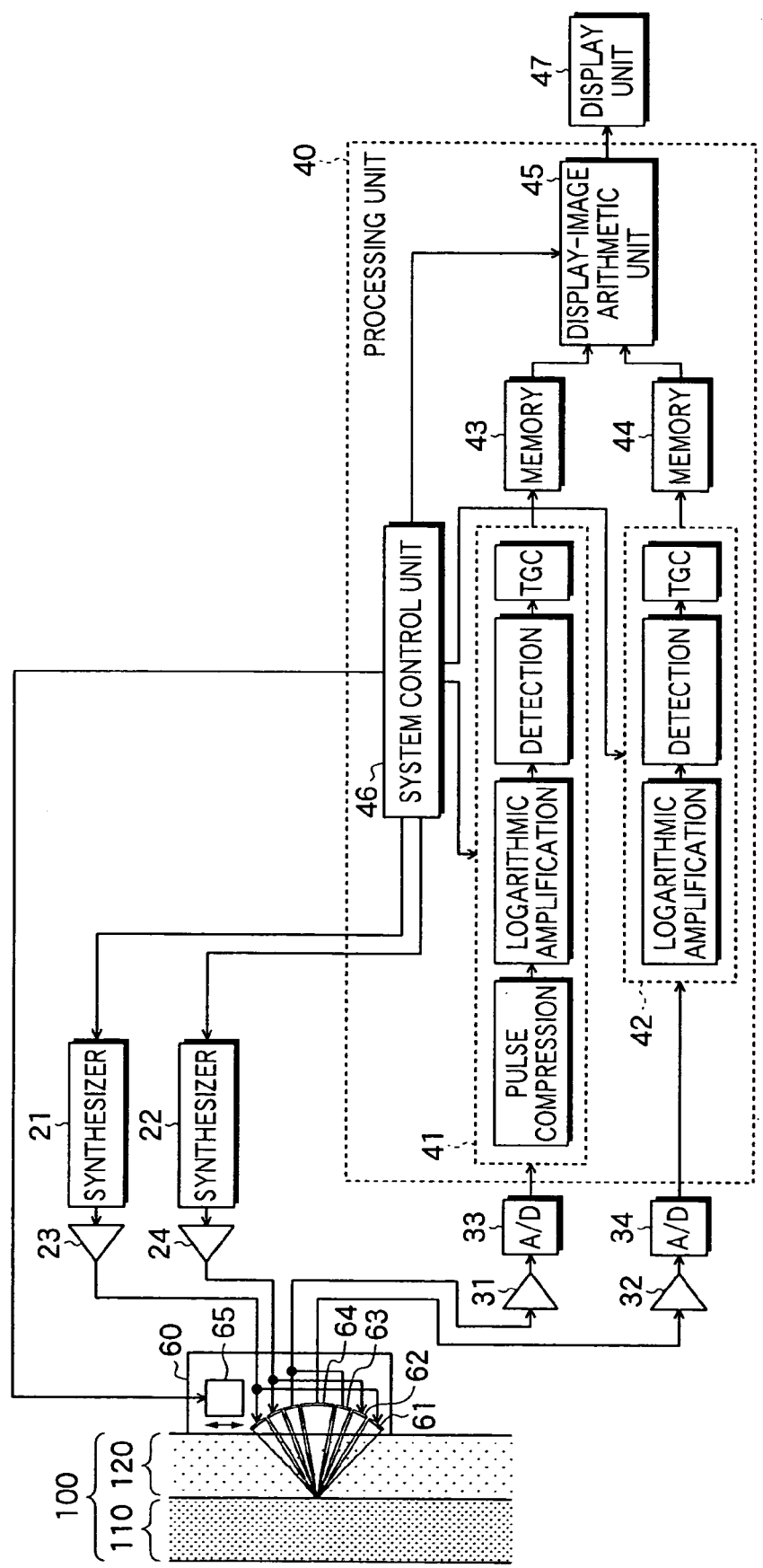
FIG. 11 is a block diagram showing the configuration of an ultrasonic transmission/reception apparatus according to the fourth embodiment of the invention.

Next, an ultrasonic transmission/reception apparatus according to the fourth embodiment of the invention will be described with reference to FIG. 3, FIG. 11, and FIGS. 12A and 12B. FIG. 11 is a block diagram showing the configuration of the ultrasonic transmission/reception apparatus according to this embodiment.

As shown in FIG. 11, the ultrasonic transmission/reception apparatus includes an ultrasonic probe 60 which is used in touch with the object 100. The ultrasonic probe 60 includes transmission elements 61 and 62 for ultrasonic waves, reception elements 63 and 64 for an ultrasonic echo and a vibro-acoustic sound, and a mechanical stage 65. The remaining configuration is the same as in the ultrasonic transmission/reception apparatus shown in FIG. 1.

Each of the transmission elements 61 and 62 and the reception elements 63 and 64 is an ultrasonic transducer in which electrodes are formed on a piezoelectric element made of PZT or the like.

The transmission elements 61 and 62 are connected to the transmission-side circuit of the ultrasonic transmission/reception apparatus, and they are respectively used for transmitting the ultrasonic waves US1 and US2 toward the imaging region of the object 100. Besides, the reception elements 63 and 64 are connected to the reception-side circuit of the ultrasonic transmission/reception apparatus, and they are respectively used for receiving the ultrasonic echo and the vibro-acoustic sound which propagate within the object 100.

Figure 12A:
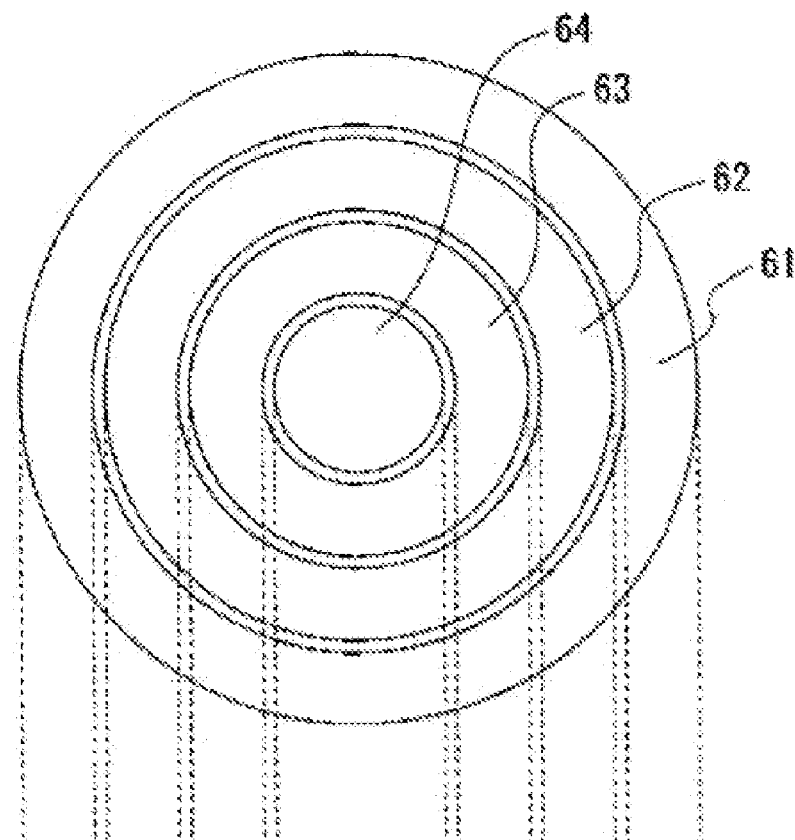
FIG. 12A is a front view showing transmission elements 61 and 62 and reception elements 63 and 64 shown in FIG. 11, on an enlarged scale.
Figure 12B:
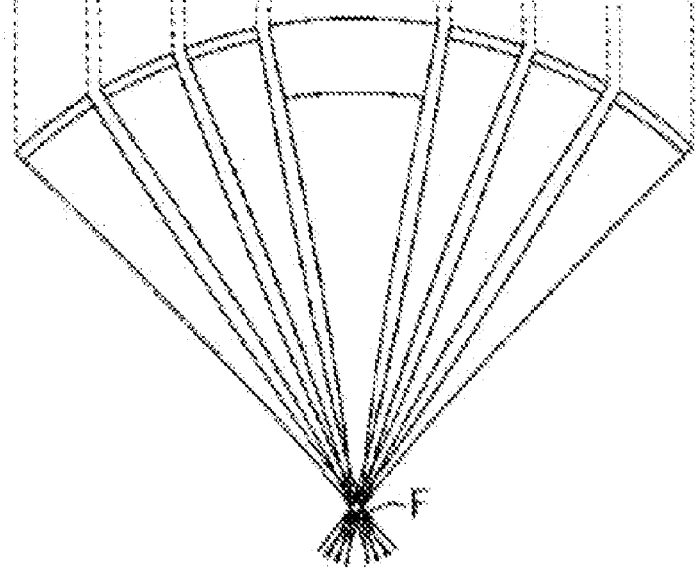
FIG. 12B is a sectional view corresponding to FIG. 12A.

FIG. 12A is a front view showing the transmission elements 61 and 62 and the reception elements 63 and 64 shown in FIG. 11, on an enlarged scale, while FIG. 12B is a sectional view corresponding to FIG. 12A. The transmission elements 61 and 62 and the reception element 63 which have annular shapes, and the reception element 64 which has a circular shape, are arranged so as to form concentric circles and to constitute a coaxial annular array. Incidentally, the reception element 64 may well be formed into an annular shape. Owing to such a coaxial arrangement of the transmission elements and reception elements, the foci F of the two ultrasonic beams respectively transmitted from the transmission elements 61 and 62 can be easily brought into coincidence, and the vibro-acoustic sound whose reception focus is held in coincidence with the generation region thereof can be received by the reception element 64.

The transmission elements 61 and 62, and the reception elements 63 and 64 have the frequency characteristics as shown in FIG. 3. More specifically, the transmission elements 61 and 62 for the ultrasonic waves are set so as to exhibit the highest sensitivity in the megahertz band (for example, 3 MHz-5 MHz). Besides, the reception element 63 has the substantially constant reception sensitivity in the frequency band of several hundred kHz—several tens MHz. Further, the reception element 64 has the substantially constant reception sensitivity in the frequency band of several kHz—several hundred kHz.

The mechanical stage 65 moves the annular array including the transmission elements 61 and 62 and the reception elements 63 and 64, whereby the object 100 is linearly scanned with the ultrasonic waves to be transmitted.

According to the ultrasonic transmission/reception apparatus of this embodiment, the transmission elements for the ultrasonic waves and the reception elements for the ultrasonic echo and the vibro-acoustic sound are integrated in the single ultrasonic probe 60, so that the positional relationship between the reception element 64 and the region where the vibro-acoustic sound is generated in the object 100 is always held constant. Accordingly, even in a case where the ultrasonic probe 60 is moved to scan the object 100 with the ultrasonic waves, an intensity correction corresponding to the distance between the generation region of the vibro-acoustic sound and the reception element 64 need not be made in processing the detection signal of the vibro-acoustic sound.

Next, an ultrasonic transmission/reception apparatus according to the fifth embodiment of the invention will be described. FIG. 13 is a model diagram showing part of the ultrasonic transmission/reception apparatus according to this embodiment. The ultrasonic transmission/reception apparatus according to this embodiment includes an ultrasonic probe 70 instead of the ultrasonic probe 60 shown in FIG. 11. The remaining configuration is the same as in the ultrasonic transmission/reception apparatus shown in FIG. 11.

Likewise to the ultrasonic probe 60 shown in FIG. 11, the ultrasonic probe 70 includes transmission elements 71 and 72 and reception elements 73 and 74 which constitute a coaxial annular array. Besides, the ultrasonic probe 70 includes a mechanical stage 75 which oscillates the annular array in accordance with the control of a system control unit 46.

In the ultrasonic transmission/reception apparatus according to this embodiment, the annular array is oscillated by the mechanical stage 75, whereby the object 100 can be sector-scanned with ultrasonic waves US1 and US2 which are respectively transmitted from the transmission elements 71 and 72.

Figure 14:
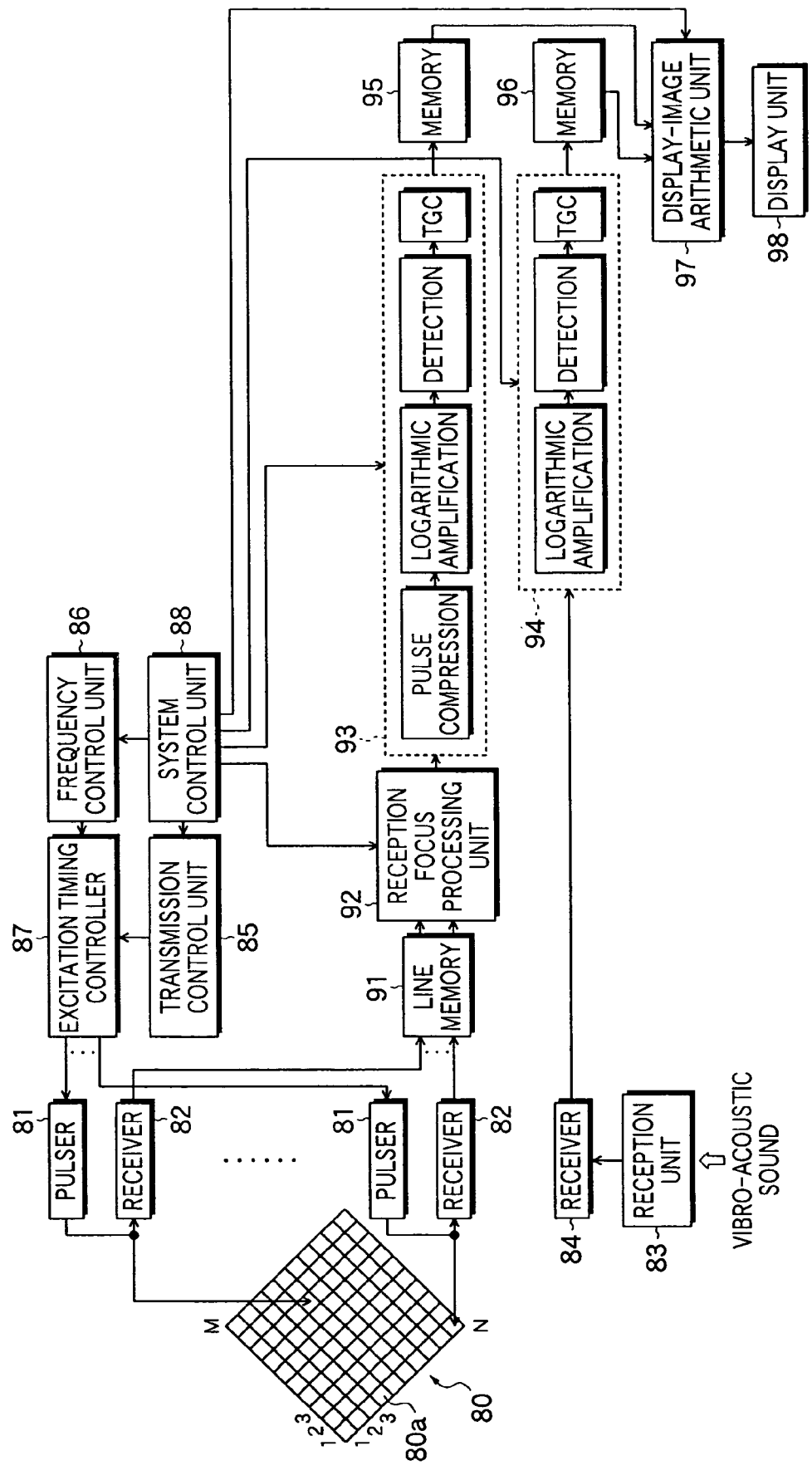
FIG. 14 is a block diagram showing the configuration of an ultrasonic transmission/reception apparatus according to the sixth embodiment of the invention.

Next, an ultrasonic transmission/reception apparatus according to the sixth embodiment of the invention will be described. FIG. 14 is a block diagram showing the configuration of the ultrasonic transmission/reception apparatus according to this embodiment. The ultrasonic transmission/reception apparatus according to this embodiment scans the object with ultrasonic waves by electronically controlling ultrasonic transducers which transmit the ultrasonic waves.

The ultrasonic transmission/reception apparatus includes an ultrasonic transducer array 80 which includes a plurality of (M×N) ultrasonic transducers 80a arrayed in the shape of, for example, a two-dimensional matrix, and a plurality of pairs of pulser circuits 81 and receivers 82 which are connected to the respective ultrasonic transducers 80a. Each of the plurality of ultrasonic transducers 80a includes a piezoelectric element made of PZT or the like, and it transmits an ultrasonic beam on the basis of an applied drive signal, while it receives an ultrasonic wave (ultrasonic echo) reflected from the object, so as to output a detection signal.

Each of the pulser circuits 81 outputs the drive signal to the corresponding ultrasonic transducer 80a in accordance with an excitation signal which is fed from an excitation timing controller 87 as will be explained later. Used as the pulser circuit 81 is a high-speed pulser circuit which can continuously output the drive signals at a high repetition frequency (for example, 3 MHz-10 MHz). Each of the receivers 82 pre-amplifies the detection signal of the ultrasonic echo outputted from the corresponding ultrasonic transducer 80a, and it converts the detection signal into a digital signal, which is outputted to a line memory 91.

Besides, the ultrasonic transmission/reception apparatus includes a reception unit 83 which receives a vibro-acoustic sound from the object and outputs the detection signal thereof. The reception unit 83 includes a reception element which exhibits a substantially constant reception sensitivity in a frequency band of, for example, several kHz—several hundred kHz. A receiver 84 is connected to the reception unit 83, and the detection signal of the vibro-acoustic sound as outputted from the reception unit 83 is pre-amplified and is converted into a digital signal in the receiver 84 so as to output the digital signal to a processing unit 94.

Besides, the ultrasonic transmission/reception apparatus includes a transmission control unit 85, a frequency control unit 86, the excitation timing controller 87, and a system control unit 88.

Figure 15:
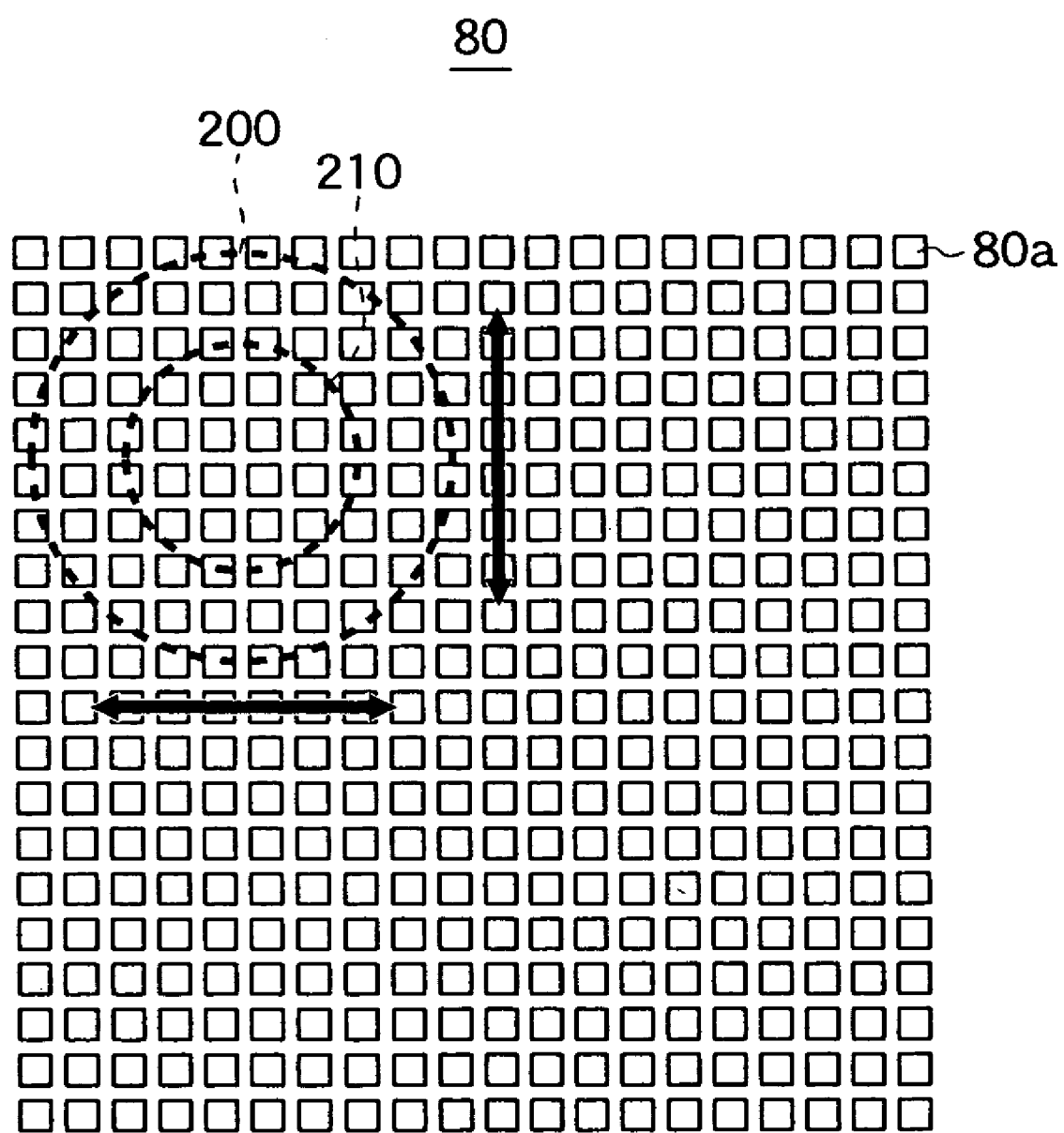
FIG. 15 is a diagram showing ultrasonic transducers which are selected by a transmission control unit, from within an ultrasonic transducer array shown in FIG. 14.

The transmission control unit 85 selects first and second groups of ultrasonic transducers for use in the transmissions of ultrasonic waves, from among the plurality of ultrasonic transducers 80a included in the ultrasonic transducer array 80. Here, FIG. 15 is a plan view showing the ultrasonic transducer array 80. As shown in FIG. 15 by way of example, the ultrasonic transducers included in an annular region 200 are selected as the first group of ultrasonic transducers, and the ultrasonic transducers included in a circular region 210 are selected as the second group of ultrasonic transducers. Besides, the transmission control unit 85 may well give predetermined delays to the first and second groups of ultrasonic transducers, respectively, so that an ultrasonic beam formed by the synthesis of the ultrasonic waves transmitted from the first and second groups of ultrasonic transducers may form a focus at a desired depth.

The frequency control unit 86 controls the excitation timing controller 87 so that a chirp waveform which has a frequency f1(t) changing from a value f1L to a value f1H rectilinearly with time may be transmitted from the first group of ultrasonic transducers, while a chirp waveform which has a frequency f2(t) changing from a value f2L to a value f2H rectilinearly with time may be transmitted from the second group of ultrasonic transducers.

The excitation timing controller 87 is constructed of, for example, a pattern generator, and it feeds the plurality of excitation signals to the pulser circuits 81 corresponding respectively to the selected first and second groups of ultrasonic transducers, at a predetermined timing.

When fed with the drive signals from the plurality of pulser circuits 81, the selected first and second groups of ultrasonic transducers generate ultrasonic pulses on the basis of the drive signals outputted from the corresponding pulser circuits 81. Owing to the synthesis of the ultrasonic pulses, the ultrasonic beam which forms the focus at the desired depth is transmitted to the object 100.

The system control unit 88 controls the various units of the ultrasonic transmission/reception apparatus.

Further, the ultrasonic transmission/reception apparatus includes the line memory 91, a reception focus processing unit 92, processing units 93 and 94, memories 95 and 96, a display-image arithmetic unit 97, and a display unit 98.

The line memory 91 has a plurality of lines corresponding respectively to the plurality of receivers 82, and it stores therein the detection data of the ultrasonic echoes outputted from the receivers 82, in time series for the respective lines.

The reception focus processing unit 92 performs arithmetic processing for matching the phases of the detection data of the ultrasonic echoes, that is, reception focus processing. More specifically, the reception focus processing unit 92 gives desired delays to the detection data of the plurality of ultrasonic echoes stored in the line memory 91 and then adds up the delayed detection data.

The processing unit 93 performs signal processing such as pulse compression, logarithmic amplification, detection and TGC amplification, for the detection data of the ultrasonic echoes subjected to the reception focus processing by the reception focus processing unit 92. Thus, sound ray data which represent ultrasonic wave information along a desired scan line are generated.

The processing unit 94 performs signal processing such as logarithmic amplification, detection and TGC amplification, for the detection data of the inputted vibro-acoustic sounds. Thus, sound ray data which correspond to the received vibro-acoustic sounds are generated.

The memories 95 and 96 store the generated sound ray data in predetermined storage areas. The sound ray data respectively stored in the memories 95 and 96 constitute surface data which represent one section in the object.

The display-image arithmetic unit 97 converts a scan format for the sound ray data (surface data) respectively stored in the memories 95 and 96, thereby to generate B-mode image data. The display unit 98 is a display device, for example, a CRT or an LCD, and it displays an ultrasonic image on the basis of the B-mode image data generated by the display-image arithmetic unit 97.

In the ultrasonic transmission/reception apparatus according to this embodiment, the transmission positions of the ultrasonic waves are altered by altering the selection regions in the ultrasonic transducer array 80 by means of the transmission control unit 85, so that the object is linearly scanned with the transmitted ultrasonic waves. However, the transmission directions of the ultrasonic waves may well be altered by altering the delay times which are given to the selected first and second groups of ultrasonic transducers, without altering the transmission positions of the ultrasonic waves. Thus, the object is sector-scanned.

In the ultrasonic transmission/reception apparatus according to this embodiment, the reception unit for receiving the vibro-acoustic sounds has been disposed separately from the ultrasonic transducer array, but the vibro-acoustic sounds may well be received in the ultrasonic transducer array. In that case, ultrasonic transducers for receiving vibro-acoustic sounds, each of which has a reception sensitivity in a frequency band near several kHz—several hundred kHz should desirably be arrayed at suitable intervals in the ultrasonic transducer array. Also, in that case, a phase control unit which subjects the detection data of the received vibro-acoustic sounds to phase matching should desirably be further disposed.

Figure 16:
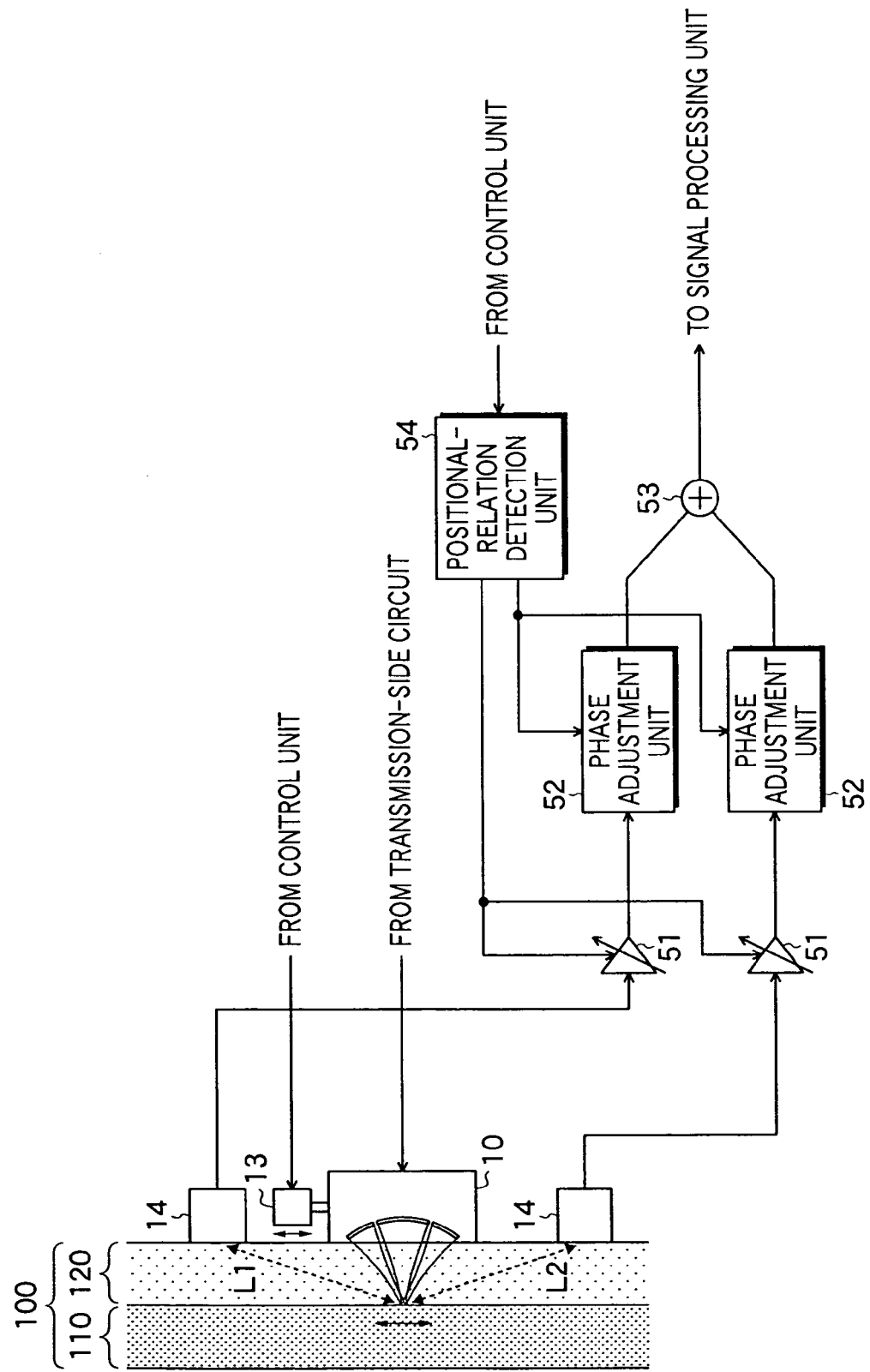
FIG. 16 is a block diagram showing the configuration of an ultrasonic transmission/reception apparatus according to the seventh embodiment of the invention.

Next, an ultrasonic transmission/reception apparatus according to the seventh embodiment of the invention will be described. FIG. 16 is a block diagram showing part of the ultrasonic transmission/reception apparatus according to this embodiment.

The ultrasonic transmission/reception apparatus according to this embodiment includes a plurality of reception units 14. It includes preamplifiers 51 respectively connected to the plurality of reception units 14, a plurality of phase adjustment units 52, an addition unit 53, and a positional-relation detection unit 54, instead of the preamplifiers 31 and 32, and the A/D converters 33 and 34 in the ultrasonic transmission/reception apparatus shown in FIG. 1. The remaining configuration is the same as in the ultrasonic transmission/reception apparatus shown in FIG. 1.

In the ultrasonic transmission/reception apparatus according to this embodiment, the positions of the plurality of reception units 14 are fixed, and an ultrasonic transmission unit 10 is moved by a mechanical stage 13, whereby the object is linearly scanned. On that occasion, the positional-relation detection unit 54 detects the positional relations L1 and L2 between the positions of foci formed by transmitted ultrasonic waves, that is, the generation region of a vibro-acoustic sound, and the respective reception units 14. Further, the positional-relation detection unit 54 regulates the gains of the plurality of preamplifiers 51 for amplifying detection signals received by the reception units 14, on the basis of the detected positional relations L1 and L2, respectively, and it sets phase shifts to be given to the detection signals in the plurality of phase adjustment units 52, respectively. Thus, the detection signals outputted from the respective reception units 14 are subjected to intensity corrections corresponding to the positional relations, and they have their phases adjusted in the respective phase adjustment units 52. Further, the detection signals outputted from the plurality of phase adjustment units 52 are added up in the addition unit 53, whereby reception focus processing is performed so as to form a focus at the generation position of the vibro-acoustic sound.

In this manner, according to the ultrasonic transmission/reception apparatus of this embodiment, the vibro-acoustic sound is received using the plurality of reception units 14, and hence, a large detection signal can be acquired.

Besides, in each of the first-seventh embodiments of the invention as thus far described, the vibro-acoustic sound has been generated by transmitting the two ultrasonic waves of different frequencies. However, a method of generating the vibro-acoustic sound is not restricted to the method explained above. Mentioned as other methods are, for example, a method wherein the amplitude of an ultrasonic wave of single frequency is modulated as disclosed in U.S. Pat. No. 5,921,928, a method wherein amplitude-modulated ultrasonic waves of single frequency are intermittently transmitted, and a method wherein an ultrasonic wave of low frequency is pumped and is stimulated with an ultrasonic wave of high frequency, thereby to cause a nonlinear phenomenon, as disclosed in U.S. Pat. No. 6,408,679.

Besides, in receiving the vibro-acoustic sound, Doppler scan may well be performed as disclosed in FIG. 5 of U.S. Pat. No. 5,903,516.

The invention claimed is:

1. An ultrasonic transmission/reception apparatus comprising:

first and second ultrasonic transmission means for operating in accordance with applied drive signals, respectively;

drive-signal generation means for generating the drive signals which are respectively applied to said first and second ultrasonic transmission means;

control means for controlling said drive-signal generation means so that a first ultrasonic wave may be transmitted from the first ultrasonic transmission means while its frequency is being swept, and that a second ultrasonic wave may be transmitted from the second ultrasonic transmission means while its frequency is being swept with a predetermined difference frequency held relative to a frequency of the first ultrasonic wave;

first reception means for receiving an ultrasonic echo caused by reflection of the first or second ultrasonic wave in an object to be inspected, so as to output a first detection signal;

second reception means for receiving an acoustic wave or an ultrasonic wave which has been generated from a predetermined region within the object by projecting the first and second ultrasonic waves toward the region, and which has a frequency corresponding to a difference frequency between frequencies of the first and second ultrasonic waves, so as to output a second detection signal;

first signal processing means for subjecting the first detection signal outputted from said first reception means, to pulse compression processing as signal processing;

second signal processing means for subjecting the second detection signal outputted from said second reception means, to predetermined signal processing; and image data generation means for generating image data representative of an ultrasonic image, on the basis of the first and second detection signals subjected to the signal processing by said first and second signal processing means.

2. An ultrasonic transmission/reception apparatus according to claim 1, wherein said image data generation means generates image data representative of an ultrasonic image on interior of a bone on the basis of the second detection signal outputted from said second reception means.

3. An ultrasonic transmission/reception apparatus according to claim 1, further comprising:

drive means for mechanically driving said second reception means so that the first and second ultrasonic waves may scan the object while a positional relation between the region and said second reception means is held constant.

4. An ultrasonic transmission/reception apparatus according to claim 1, wherein:

said first and second ultrasonic transmission means and said first reception means are constituted by using same elements which transmit and receive the ultrasonic waves; and said apparatus further comprises transmission/reception changeover means for changing-over transmissions of the first and second ultrasonic waves and receptions of the ultrasonic echoes in the elements is further comprised.

5. An ultrasonic transmission/reception apparatus according to claim 1, wherein said first and second ultrasonic transmission means and said first and second reception means are included in ultrasonic probe means for coming into touch with the object.

6. An ultrasonic transmission/reception apparatus according to claim 5, wherein said ultrasonic probe means includes drive means for mechanically oscillating said first and second ultrasonic transmission means and said first and second reception means.

7. An ultrasonic transmission/reception apparatus according to claim 1, wherein:

said first and second ultrasonic transmission means and said first reception means are constructed of an ultrasonic transducer array which includes a plurality of ultrasonic transducers arrayed in a shape of a two-dimensional matrix; and said plurality of ultrasonic transducers include a first group of ultrasonic transducers for transmitting the first ultrasonic wave, and a second group of ultrasonic transducers for transmitting the second ultrasonic wave.

8. An ultrasonic transmission/reception apparatus according to claim 1, further comprising:

at least one third reception means for receiving the acoustic wave which has been generated from the predetermined region in the object by projecting the first and second ultrasonic waves toward the region, and which has the frequency corresponding to the difference frequency between the frequencies of the first and second ultrasonic waves, so as to output a third detection signal; and means for performing reception focus processing for the second detection signal outputted from said second reception means and the third detection signal outputted from said at least one third reception means, so that the acoustic wave received by said second reception means and the acoustic wave received by said at least one third reception means may form a focus in the region.

* * * * *